(12) United States Patent
Morrissey et al.

(10) Patent No.: US 10,201,579 B2
(45) Date of Patent: *Feb. 12, 2019

(54) COMPOSITIONS FOR REDUCING ENVIRONMENTAL SENSITIVITY AND REGULATING IMMUNE FUNCTION

(71) Applicants: Edward Stephen Morrissey, Boulder, CO (US); Ruotao Wang, Beijing (CN)

(72) Inventors: Edward Stephen Morrissey, Boulder, CO (US); Ruotao Wang, Beijing (CN)

(73) Assignee: Eclipta LLC, Central Point, OR (US)

( * ) Notice: Subject to any disclaimer, the term of this patent is extended or adjusted under 35 U.S.C. 154(b) by 507 days.

This patent is subject to a terminal disclaimer.

(21) Appl. No.: 14/997,953

(22) Filed: Jan. 18, 2016

(65) Prior Publication Data

US 2016/0235800 A1 Aug. 18, 2016

Related U.S. Application Data

(63) Continuation of application No. 14/515,955, filed on Oct. 16, 2014, now Pat. No. 9,238,050.

(51) Int. Cl.

| | |
|---|---|
| *A61K 36/487* | (2006.01) |
| *A61K 36/539* | (2006.01) |
| *A61K 36/28* | (2006.01) |
| *A61K 36/744* | (2006.01) |
| *A23L 1/00* | (2006.01) |
| *A23L 1/30* | (2006.01) |
| *A61K 9/00* | (2006.01) |
| *A61K 9/20* | (2006.01) |
| *A61K 9/48* | (2006.01) |

(52) U.S. Cl.
CPC .......... *A61K 36/487* (2013.01); *A23L 1/0073* (2013.01); *A23L 1/3002* (2013.01); *A61K 9/0053* (2013.01); *A61K 9/0095* (2013.01); *A61K 9/20* (2013.01); *A61K 9/48* (2013.01); *A61K 36/28* (2013.01); *A61K 36/539* (2013.01); *A61K 36/744* (2013.01); *A23V 2002/00* (2013.01)

(58) Field of Classification Search
CPC .. A61K 2300/00; A61K 36/487; A61K 36/28; A61K 36/539; A61K 36/744; A61K 9/0053; A61K 9/0095; A61K 9/20; A61K 9/48; A23L 1/0073; A23L 1/3002; A23V 2002/00

See application file for complete search history.

(56) References Cited

U.S. PATENT DOCUMENTS

| | | | |
|---|---|---|---|
| 9,238,050 B1 * | 1/2016 | Morrissey ............ | A61K 36/539 |
| 2004/0208941 A1 * | 10/2004 | Riley ....................... | A61K 8/67 424/725 |

FOREIGN PATENT DOCUMENTS

CN 102430099 A 5/2012

\* cited by examiner

*Primary Examiner* — Aaron J Kosar

(74) *Attorney, Agent, or Firm* — Mersenne Law

(57) ABSTRACT

The present invention is directed to compositions for improving immune function and sensitivities to the natural and manmade environment that include ingredients from natural sources. It is further directed to methods of administering the compositions and kits containing the compositions. In a composition aspect, the composition is for regulating immune function and non-immune related sensitivities. It consists essentially of: 2 weight percent to 95 weight percent *Psoralea;* 2 weight percent to 95 weight percent *Scutellaria;* and 2 weight percent to 95 weight percent *Xanthium*. The *Scutellaria* portion may be replaced by *Gardenia* (in equal measure), or by a mixture of *Scutellaria* and *Gardenia*.

16 Claims, No Drawings

COMPOSITIONS FOR REDUCING ENVIRONMENTAL SENSITIVITY AND REGULATING IMMUNE FUNCTION

CONTINUITY AND CLAIM OF PRIORITY

This U.S. patent application claims priority to U.S. patent application Ser. No. 14/515,955 filed 16 Oct. 2014 (now U.S. Pat. No. 9,238,050 issued 19 Jan. 2016).

FIELD

The present invention is directed to compositions for regulating the body's reaction to elements and conditions of the environment that may trigger immune and/or non-immune mediated reactions or sensitivities. Methods of administering the compositions and kits containing the compositions are also described. Embodiments are specifically directed to compositions that include ingredients from natural sources.

BACKGROUND

An eleven-ingredient immune-support formula was developed. The formula was shown to aid in the reduction of symptoms related to exposure to allergens and other elements of the environment that trigger immune and non-immune related symptoms affecting body systems from respiratory, digestive, as well as the dermis and epidermis. The ingredients of the formula are as follows: *Psoralea* fruit; Skullcap root; *Xanthium* fruit; *Chrysanthemum* flower; *Gardenia* fruit; Betelnut husk; *Schisandra* berry; Bupleurum root; Jujube seed; Plantain seed; and, Schizonepeta aerial parts.

Investigations and experience with the eleven-ingredient formula showed no primary ingredient in the formula or any one particularly responsible for many of the observed benefits. All ingredients were thought to play a supporting role in the composition.

While the prior-art formulation affords desirable outcomes with respect to environmental sensitivities and/or reactions, it is rather large in volume and relatively expensive to make. Furthermore, in view of the large number of ingredients, it was found to be difficult to hit consistency and standardized functionality (biologic activity) targets. An improved formulation that is more compact (less voluminous) and less expensive to make, but nevertheless offers similar beneficial effects against environmental sensitivities ranging from foods to pollen, dust, temperatures, air pollution, and other environmental irritants, may be of significant value in this field.

SUMMARY

The present invention is directed to compositions for improving immune and non-immune mediated environmental sensitivities that include ingredients from natural sources. It is further directed to methods of administering the compositions and kits containing the compositions.

The inventive compositions for regulating immune and non-immune related environmental sensitivities consist essentially of: 2 weight percent to 95 weight percent *Psoralea*; 2 weight percent to 95 weight percent *Xanthium*; and 2 weight percent to 95 weight percent of a third ingredient, which may be *Gardenia, Scutellaria*, or a mixture of these two ingredients (the mixture present at about 2 weight percent to 95 weight percent).

Formulations for packaging/delivering the inventive compositions for treating environmental sensitivities are also described and claimed. All of the delivery formulations include an effective dose the inventive composition, with non-active ingredients to permit the composition to be manufactured and provided in various convenient forms.

Embodiments of the inventive composition may be supplied as a kit, comprising either subsets of the active ingredients or the pre-mixed active ingredients, plus a set of instructions for compounding (if necessary), applying, evaluating and adjusting the dosage of the composition.

DETAILED DESCRIPTION

The present invention is directed to compositions for improving immune function and non-immune related environmental sensitivities that include ingredients from natural sources. It is further directed to methods of administering the compositions and kits containing the compositions.

Compositions

The compositions of the present invention include *Psoralea, Scutellaria* (and/or *Gardenia*, as discussed below) and *Xanthium* as active ingredients in various ratios. Typically, the composition comprises *Psoralea* (2-95 wt. %), *Scutellaria* (2-95 wt. %), and

*Xanthium* (2-95 wt. %) as active ingredients. Nonlimiting examples of acceptable ratios of active ingredients present in effective compositions according to an embodiment are provided below:

| Psoralea (% by weight) | Scutellaria (% by weight) | Xanthium (% by weight) | Psoralea (% by weight) | Scutellaria (% by weight) | Xanthium (% by weight) |
|---|---|---|---|---|---|
| 95 wt. % | 2 wt. % | 3 wt. % | 40 wt. % | 45 wt. % | 15 wt. % |
| 95 wt. % | 3 wt. % | 2 wt. % | 40 wt. % | 40 wt. % | 20 wt. % |
| 90 wt. % | 5 wt. % | 5 wt. % | 40 wt. % | 35 wt. % | 25 wt. % |
| 85 wt. % | 5 wt. % | 10 wt. % | 40 wt. % | 30 wt. % | 30 wt. % |
| 85 wt. % | 10 wt. % | 5 wt. % | 40 wt. % | 25 wt. % | 35 wt. % |
| 80 wt. % | 10 wt. % | 10 wt. % | 40 wt. % | 20 wt. % | 40 wt. % |
| 75 wt. % | 10 wt. % | 15 wt. % | 40 wt. % | 15 wt. % | 45 wt. % |
| 75 wt. % | 15 wt. % | 10 wt. % | 40 wt. % | 10 wt. % | 50 wt. % |
| 70 wt. % | 20 wt. % | 10 wt. % | 35 wt. % | 55 wt. % | 10 wt. % |
| 70 wt. % | 15 wt. % | 15 wt. % | 35 wt. % | 50 wt. % | 15 wt. % |
| 70 wt. % | 10 wt. % | 20 wt. % | 35 wt. % | 45 wt. % | 20 wt. % |
| 65 wt. % | 25 wt. % | 10 wt. % | 35 wt. % | 40 wt. % | 25 wt. % |
| 65 wt. % | 20 wt. % | 15 wt. % | 35 wt. % | 35 wt. % | 30 wt. % |
| 65 wt. % | 15 wt. % | 20 wt. % | 35 wt. % | 30 wt. % | 35 wt. % |
| 65 wt. % | 10 wt. % | 25 wt. % | 35 wt. % | 25 wt. % | 40 wt. % |
| 60 wt. % | 30 wt. % | 10 wt. % | 35 wt. % | 20 wt. % | 45 wt. % |
| 60 wt. % | 25 wt. % | 15 wt. % | 35 wt. % | 15 wt. % | 50 wt. % |

| Psoralea (% by weight) | Scutellaria (% by weight) | Xanthium (% by weight) | Psoralea (% by weight) | Scutellaria (% by weight) | Xanthium (% by weight) |
|---|---|---|---|---|---|
| 60 wt. % | 20 wt. % | 20 wt. % | 35 wt. % | 10 wt. % | 55 wt. % |
| 60 wt. % | 15 wt. % | 25 wt. % | 30 wt. % | 60 wt. % | 10 wt. % |
| 60 wt. % | 10 wt. % | 30 wt. % | 30 wt. % | 55 wt. % | 15 wt. % |
| 55 wt. % | 35 wt. % | 10 wt. % | 30 wt. % | 50 wt. % | 20 wt. % |
| 55 wt. % | 30 wt. % | 15 wt. % | 30 wt. % | 45 wt. % | 25 wt. % |
| 55 wt. % | 25 wt. % | 20 wt. % | 30 wt. % | 40 wt. % | 30 wt. % |
| 55 wt. % | 20 wt. % | 25 wt. % | 30 wt. % | 35 wt. % | 35 wt. % |
| 55 wt. % | 15 wt. % | 30 wt. % | 30 wt. % | 30 wt. % | 40 wt. % |
| 55 wt. % | 10 wt. % | 35 wt. % | 30 wt. % | 25 wt. % | 45 wt. % |
| 50 wt. % | 40 wt. % | 10 wt. % | 30 wt. % | 20 wt. % | 50 wt. % |
| 50 wt. % | 35 wt. % | 15 wt. % | 30 wt. % | 15 wt. % | 55 wt. % |
| 50 wt. % | 30 wt. % | 20 wt. % | 30 wt. % | 10 wt. % | 60 wt. % |
| 50 wt. % | 25 wt. % | 25 wt. % | 25 wt. % | 65 wt. % | 10 wt. % |
| 50 wt. % | 20 wt. % | 30 wt. % | 25 wt. % | 60 wt. % | 15 wt. % |
| 50 wt. % | 15 wt. % | 35 wt. % | 25 wt. % | 55 wt. % | 20 wt. % |
| 50 wt. % | 10 wt. % | 40 wt. % | 25 wt. % | 50 wt. % | 25 wt. % |
| 45 wt. % | 45 wt. % | 10 wt. % | 25 wt. % | 45 wt. % | 30 wt. % |
| 45 wt. % | 40 wt. % | 15 wt. % | 25 wt. % | 40 wt. % | 35 wt. % |
| 45 wt. % | 35 wt. % | 20 wt. % | 25 wt. % | 35 wt. % | 40 wt. % |
| 45 wt. % | 30 wt. % | 25 wt. % | 25 wt. % | 30 wt. % | 45 wt. % |
| 45 wt. % | 25 wt. % | 30 wt. % | 25 wt. % | 25 wt. % | 50 wt. % |
| 45 wt. % | 20 wt. % | 35 wt. % | 25 wt. % | 20 wt. % | 55 wt. % |
| 45 wt. % | 15 wt. % | 40 wt. % | 25 wt. % | 15 wt. % | 60 wt. % |
| 45 wt. % | 10 wt. % | 45 wt. % | 25 wt. % | 10 wt. % | 65 wt. % |
| 40 wt. % | 50 wt. % | 10 wt. % | 20 wt. % | 70 wt. % | 10 wt. % |
| 20 wt. % | 65 wt. % | 15 wt. % | 2 wt. % | 95 wt. % | 3 wt. % |
| 20 wt. % | 60 wt. % | 20 wt. % | 3 wt. % | 95 wt. % | 2 wt. % |
| 20 wt. % | 55 wt. % | 25 wt. % | 5 wt. % | 90 wt. % | 5 wt. % |
| 20 wt. % | 50 wt. % | 30 wt. % | 5 wt. % | 85 wt. % | 10 wt. % |
| 20 wt. % | 45 wt. % | 35 wt. % | 10 wt. % | 85 wt. % | 5 wt. % |
| 20 wt. % | 40 wt. % | 40 wt. % | 10 wt. % | 80 wt. % | 10 wt. % |
| 20 wt. % | 35 wt. % | 45 wt. % | 10 wt. % | 75 wt. % | 15 wt. % |
| 20 wt. % | 30 wt. % | 50 wt. % | 10 wt. % | 70 wt. % | 20 wt. % |
| 20 wt. % | 25 wt. % | 55 wt. % | 10 wt. % | 65 wt. % | 25 wt. % |
| 20 wt. % | 20 wt. % | 60 wt. % | 10 wt. % | 60 wt. % | 30 wt. % |
| 20 wt. % | 15 wt. % | 65 wt. % | 10 wt. % | 55 wt. % | 35 wt. % |
| 20 wt. % | 10 wt. % | 70 wt. % | 10 wt. % | 50 wt. % | 40 wt. % |
| 15 wt. % | 75 wt. % | 10 wt. % | 10 wt. % | 45 wt. % | 45 wt. % |
| 15 wt. % | 70 wt. % | 15 wt. % | 10 wt. % | 40 wt. % | 50 wt. % |
| 15 wt. % | 65 wt. % | 20 wt. % | 10 wt. % | 35 wt. % | 55 wt. % |
| 15 wt. % | 60 wt. % | 25 wt. % | 10 wt. % | 30 wt. % | 60 wt. % |
| 15 wt. % | 55 wt. % | 30 wt. % | 10 wt. % | 25 wt. % | 65 wt. % |
| 15 wt. % | 50 wt. % | 35 wt. % | 10 wt. % | 20 wt. % | 70 wt. % |
| 15 wt. % | 45 wt. % | 40 wt. % | 10 wt. % | 15 wt. % | 75 wt. % |
| 15 wt. % | 40 wt. % | 45 wt. % | 10 wt. % | 10 wt. % | 80 wt. % |
| 15 wt. % | 35 wt. % | 50 wt. % | 10 wt. % | 5 wt. % | 85 wt. % |
| 15 wt. % | 30 wt. % | 55 wt. % | 5 wt. % | 10 wt. % | 85 wt. % |
| 15 wt. % | 25 wt. % | 60 wt. % | 5 wt. % | 5 wt. % | 90 wt. % |
| 15 wt. % | 20 wt. % | 65 wt. % | 3 wt. % | 2 wt. % | 95 wt. % |
| 15 wt. % | 15 wt. % | 70 wt. % | 2 wt. % | 3 wt. % | 95 wt. % |
| 15 wt. % | 10 wt. % | 75 wt. % | | | |

The "*Scutellaria*" fraction in the composition tables may be satisfied, at least in part, by either *Scutellaria* or *Gardenia* or a mixture of *Scutellaria* and *Gardenia*. Either ingredient or a mixture of the two ingredients may be substituted for *Scutellaria* alone.

Compositions of the present invention may take different forms for delivery (i.e., ingestion), depending on the exact formulation employed. Nonlimiting examples include:

Capsules with the addition of flour, starch, modified starch, maltodextrin, cellulose, modified cellulose, protein hydrolysate, rice powder, whey powder, calcium phosphate, calcium carbonate, lactose, saccharides, sorbitol, mannitol, xylitol, stearic acid, stearate, silica, silicate, polyethylene glycol, flavors, and/or colors, among others.

Tablets with the addition of starch, modified starch, maltodextrin, cellulose, methylcellulose, ethylcellulose, hydroxypropylmethylcellulose, modified cellulose, protein hydrolysate, rice powder, whey powder, calcium phosphate, calcium carbonate, lactose, sweeteners (e.g. sucrose, fructose, glucose, corn syrup, saccharides, saccharine, sucralose, aspartame, etc.), sorbitol, mannitol, xylitol, (gum tragacanth, gum arabic, agar, guar gum, locust bean gum, karaya gum, xanthan gum, etc.) zein, saccharides, stearic acid, stearate, silica, silicate, polyethylene glycol, pharmaceutical glaze, wax, flavors, and/or colors, among others.

Powdered drink mix with the addition of starch, modified starch, maltodextrin, cellulose, modified cellulose, protein hydrolysate, whey powder, calcium phosphate, calcium carbonate, lactose, sorbitol, mannitol, xylitol, sweeteners (e.g. sucrose, fructose, glucose, corn syrup, saccharides, saccharine, sucralose, aspartame, etc.), stearic acid, stearate, silica, silicate, flavors, and/or colors, among others.

Ready-to-drink beverages with the addition of starch, modified starch, maltodextrin, cellulose, modified cellulose, protein hydrolysate, whey powder, calcium phosphate, calcium carbonate, lecithin, sweeteners (e.g. sucrose, fructose, glucose, corn syrup, saccharides, saccharine, sucralose, aspartame, etc.), sorbitol, mannitol, xylitol, silica, silicate, solvents (e.g. water, ethanol, polyethylene glycol, propylene glycol, glycerin), acidifiers (e.g. citric acid, acetic acid, malic acid, tartaric acid), citrate, preservatives (e.g. benzoic acid, benzoate, sorbic acid, sorbate, polysorbate, propionic acid, propionate, nisin), caffeine, flavors, and/or colors, among others.

Semisolids such as gu™ with the addition of starch, modified starch, maltodextrin, cellulose, modified cellulose, protein hydrolysate, whey powder, calcium phosphate, calcium carbonate, lecithin, oil, partially hydrogenated oil, fat, milk, milk solids, mono- or diglycerides, polysorbates, sorbitan monostearate, (gum tragacanth, gum arabic, agar, guar gum, locust bean gum, karaya gum, xanthan gum, etc.), sweeteners (e.g. sucrose, fructose, glucose, corn syrup, saccharides, saccharine, sucralose, aspartame, etc.), sorbitol, mannitol, xylitol, silica, silicate, solvents (e.g. water, ethanol, polyethylene glycol, propylene glycol, glycerin), acidifiers (e.g. citric acid, acetic acid, malic acid, tartaric acid), citrate, preservatives (e.g. benzoic acid, benzoate, sorbic acid, sorbate, polysorbate, propionic acid, propionate, nisin, parabens), flavors, and/or colors, among others.

Softgel capsules with the addition of lecithin, oil, wax, glycerine, gelatin, propylene glycol, polyethylene glycol, and/or colors, among others.

Food or supplement bars with the addition of flour, starch, modified starch, maltodextrin, cellulose, methylcellulose, ethylcellulose, hydroxypropylmethylcellulose, modified cellulose, protein hydrolysate, whey powder, calcium phosphate, calcium carbonate, lecithin, mono- or diglycerides, polysorbates, sorbitan monostearate, binders (gum tragacanth, gum arabic, agar, guar gum, locust bean gum, karaya gum, xanthan gum, etc.), sweeteners (e.g. sucrose, fructose, glucose, corn syrup, saccharides, saccharine, sucralose, aspartame, etc.), sorbitol, mannitol, xylitol, silica, silicate, solvents (e.g. water, ethanol, polyethylene glycol, propylene glycol, glycerin), acidifiers (e.g. citric acid, acetic acid, malic acid, tartaric acid), citrate, preservatives (e.g. benzoic acid, benzoate, sorbic acid, sorbate, polysorbate, propionic acid, propionate, nisin, BHA, BHT, EDTA, TBHQ, etc.), flavors, and/or colors, among others.

In the foregoing sample delivery forms, the active ingredients are mixed with and/or contained by ingredients or materials having no significant active properties relative to the purposes of the inventive composition. The active ingredients are measured by weight percentages relative to the total weight of active ingredients, not the total weight of active plus inactive ingredients.

Indications

Compositions of the present invention are taken by individuals experiencing a wide range of symptoms (and may be taken prophylactically as well). Characteristics of such individuals include:

a. People who are experiencing one or more symptoms of an impending or fully established allergic or non-allergic sensitivity, including structural or functional disorders such as respiratory congestion, especially nasal congestion and/or excess nasal discharge, sneezing, itchiness, scratchy throat, excessive ocular discharge, stiff neck, skin irritations, diminished breathing capacity, or post-meal digestive discomfort.

b. People who wish to take preventative measures to reduce the likelihood of experiencing environmental sensitivity reactions.

c. People who have depressed their immune system or general health status through exposure to cold weather, heightened physical exertion or other physical stresses such as physical work or exercise, sleeplessness or irregular sleep habits, emotional stress, prolonged illness, or immune function and general health degradation that naturally occurs as part of the aging process.

d. People who want to strengthen their immune and other body systems against exposure to cold weather, environmental irritants, heightened physical exertion or other physical stresses such as physical work or exercise, sleeplessness or irregular sleep habits, emotional stress, prolonged illness, or immune function and general health degradation that naturally occurs as part of the aging process. People who want to support their body's ability to healthfully adapt to an environment or improve the resilience of their health to new, changing or challenging circumstances physically, emotionally, mentally.

Typical individual consumption of the inventive composition ranges from about 450 mg to about 1800 mg of an embodiment (i.e., 450-1800 mg of active ingredients) once to three times per day, depending on the status of immune function, general health, and other factors such as exposure or activity levels.

Compositions of the present invention provide one with general well-being and improved responses to environmental irritants and dietary sensitivities. The expected benefits for a majority of those who are experiencing the symptoms of environmental sensitivities are the reduction or cessation of one or more of the symptoms. Some may experience a reversal or cessation of all symptoms within 10 to 60 minutes.

Kits

The various delivery systems for compositions of the present invention can be packaged in a number of ways as appropriate, including but not limited to:

Bottle with label and/or insert having instructions
Foil laminate pouch with instructions
Wrapper with instructions
Carton or box with instructions and/or label with instructions and/or insert with instructions Sample Instructions For prevention, Adults take 450 mg-900 mg of the formulation once a day, 4 to 5 days per week. At the first indication of the symptoms of environmental sensitivity, Adults take 900 to 1800 mg of the blend every 2 to 8 hours as needed until symptoms are significantly reduced. If you are taking a prescription medication or are pregnant or lactating, consult with your doctor before taking the formulation.

EXPERIMENTAL RESULTS

Example 1

Numerous subjects tested using the BioRim™ medium throughput method in a clinical setting over a period of years with PSX (i.e., the *Psoralea, Scutellaria* and *Xanthium* composition of an embodiment) or PGX (*Psoralea, Gardenia* and *Xanthium* of another embodiment) showed marked improvement in immune and non-immune related response to symptoms of environmental sensitivity within 10 to 60 minutes. The same subjects were tested using control, placebo and the individual ingredients of PSX/PGX. The ingredients individually had little to no effect in relieving or protecting the subjects' biological systems against environmental sensitivities. The PSX and PGX formulations of the three combined ingredients showed a significant improvement in both immune and non-immune related response in all subjects.

The applications of the present invention have been described largely by reference to specific formulations of the three active ingredients (where one of the three may be chosen from between two alternatives, or as a mixture of the two alternative ingredients). However, those of skill in the art will recognize that the active ingredients of an embodiment may be combined with other ingredients having different purposes or active mechanisms to produce a composition that provides multiple therapeutic benefits. Such compositions are understood to be captured according to the following claims.

We claim:

1. A medicinal composition for treating allergic sensitivity, consisting essentially of:
   (i) *Psoralea* as a first active ingredient, said first active ingredient present at between 2% and 95% by weight of a total weight of active ingredients;
   (ii) *Xanthium* as a second active ingredient, said second active ingredient present at between 2% and 95% by weight of the total weight of active ingredients; and
   (iii) an effective amount of a third active ingredient chosen from the group consisting of *Scutellaria, Gardenia,* and a mixture of *Scutellaria* and *Gardenia,*
   wherein the composition is in a dosage form.

2. The medicinal composition of claim 1 wherein the third active ingredient is *Scutellaria.*

3. The medicinal composition of claim 1 wherein the third active ingredient is *Gardenia.*

4. The medicinal composition of claim 1, wherein the dosage form is a capsule.

5. The medicinal composition of claim 1, wherein the dosage form is a tablet.

6. The medicinal composition of claim 1, wherein the dosage form is a powdered drink mix.

7. The medicinal composition of claim 1, wherein the dosage form is a ready-to-drink beverage.

8. The medicinal composition of claim 1, wherein dosage form is an edible semisolid.

9. The medicinal composition of claim 1, wherein the dosage form is a softgel capsule.

10. The medicinal composition of claim 1, wherein the dosage form is a food supplement bar.

11. A method for treating allergic sensitivity in a patient in need thereof comprising administering the medicinal composition of claim 1 to the patient in an amount effective to treat symptoms of the allergic sensitivity.

12. The method of claim 11 wherein the third active ingredient is *Gardenia.*

13. The method of claim 11 wherein the third active ingredient is *Scutellaria.*

14. The method of claim 11 wherein the third active ingredient is a mixture of *Gardenia* and *Scutellaria.*

15. The method of claim 11 wherein the amount of the medicinal composition is between 450 mg and 1,800 mg.

16. The method of claim 11 wherein said administering comprises administering the medicinal composition between once and thrice daily.

* * * * *